United States Patent [19]

Lawrence et al.

[11] Patent Number: 5,009,112
[45] Date of Patent: Apr. 23, 1991

[54] METHOD AND APPARATUS FOR CONDUCTING FIELD DISSIPATION AND LEACHING STUDIES

[75] Inventors: Lowell J. Lawrence, Lexington, Ky.; Luis O. Ruzo, Berkley, Calif.; Gene L. Olson, Lexington, Ky.

[73] Assignee: Pharmacology & Toxicology Research Lab., Richmond, Ky.

[21] Appl. No.: 351,916

[22] Filed: May 5, 1989

[51] Int. Cl.$^5$ .............................. G01N 1/00
[52] U.S. Cl. ..................... 73/866; 73/863.52
[58] Field of Search ............... 73/866, 865.8, 865.6, 73/863.21, 864.44, 864.45, 863.52

[56] References Cited

U.S. PATENT DOCUMENTS 4,166,720  9/1979  Weber ........................... 73/866
4,709,584 12/1987  Voll et al. .................... 73/864.44
4,844,813  7/1989  Helfgott et al. ................ 210/747

OTHER PUBLICATIONS

Richter, Goetz & Jury, William A.; "A Microlysimeter Field Study of Solute Transport through a Structured Sandy Loam Soil," 1986, 863-866.
Stauffer, R. S., & Smith, R. S.; "Variation in Soils with Respect to the Disposition of Natural Precipitation," 1937, 917-923.
Musgrave, G. W.; "A Device for Measuring Precipitation Waters Lost from the Soil as Surface Runoff, Percolation, Evaporation, and Transpiration," 1935, 391-401.

Primary Examiner—Robert Raevis
Attorney, Agent, or Firm—King & Schickli

[57] ABSTRACT

A method for conducting field dissipation and leachate studies of a test substance includes the step of positioning a boundary column for defining a soil test zone into the ground. This may be done by driving the column into the ground. Next is the step of exposing a bottom end of the column substantially without disturbing the soil in the soil test zone. This is followed by the steps of collecting leachate from the soil test zone and analyzing the leachate collected. The method also includes the steps of recovering the soil test zone substantially intact as a core sample, cutting the core sample into segments and individually analyzing the segments for test substance dissipation both quantitatively and qualitatively. The column utilized to define the soil test zone is preferably constructed from 18 or 20 gauge galvanized steel and has a diameter of from 6 to 10 inches. The leachate collection apparatus may include a funnel and a collection container that are positioned beneath the column to collect all the leachate from the soil test zone.

15 Claims, 1 Drawing Sheet

U.S. Patent        Apr. 23, 1991        5,009,112
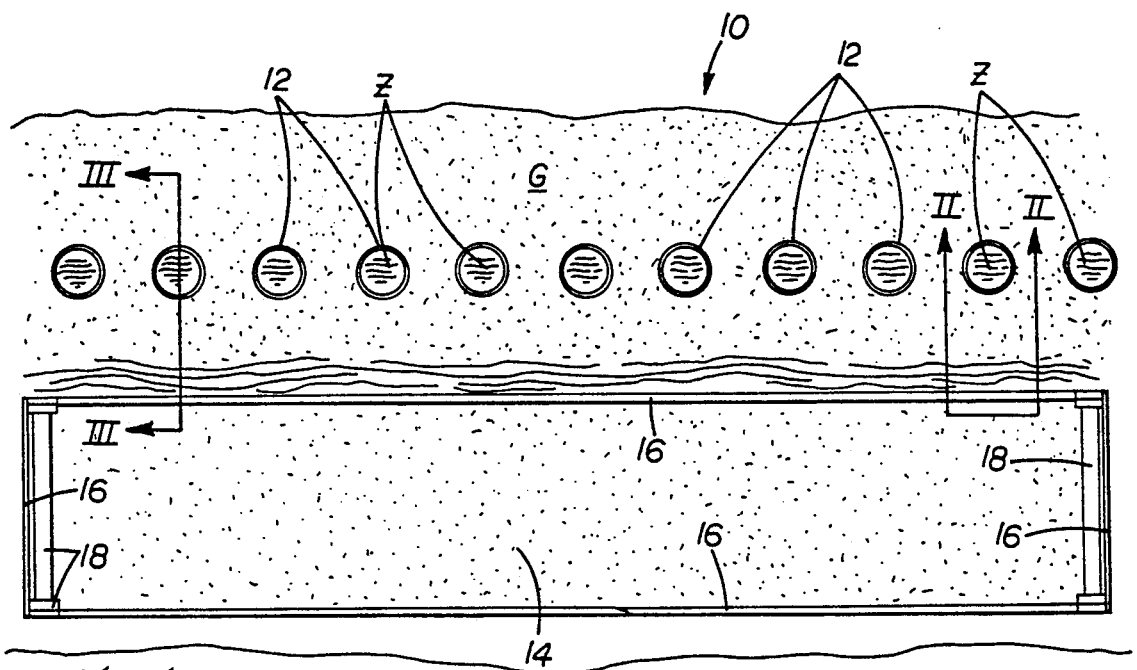
*Fig. 1*
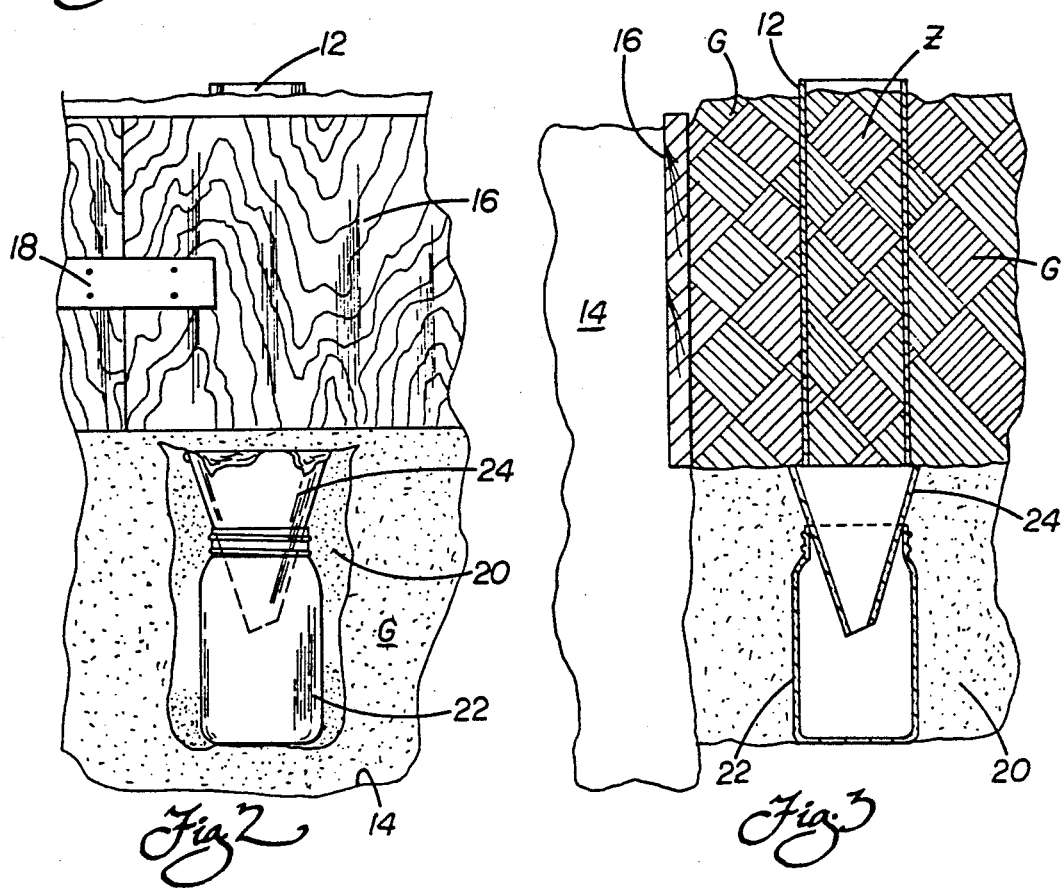
*Fig. 2*        *Fig. 3*

METHOD AND APPARATUS FOR CONDUCTING FIELD DISSIPATION AND LEACHING STUDIES

TECHNICAL FIELD

The present invention relates generally to the conducting of field dissipation studies of chemical compositions such as pesticides and, more particularly, to a method and apparatus specifically designed for this purpose.

BACKGROUND OF THE INVENTION

Over the years the agricultural and forestry industries have turned increasingly to science to help feed and house the ever increasing human population. Through the development of various herbicides, fertilizers, insecticides and pesticides for terrestial crop and forestry uses, man has been able to markedly improve the productivity of the land. The increases in crop and timber production, however, have not been obtained without suffering some adverse consequences.

More particularly, many of the herbicides, fertilizers, insecticides and pesticides that have ben developed detrimentally impact the environment in one way or another when used in certain concentrations or under certain conditions. Livestock poisonings, fish kills and other cataclysmic events have resulted. For example, many insecticides such as DDT are particularly stable and resistant to destruction by light and oxidation. With continued use, concentrations of such insecticides may build up in the environment over time to dangerous levels. This may lead to widespread death of wildlife and contamination of water supplies deleteriously affecting downstream population centers.

The problem has not gone unnoticed by the government. The Environmental Protection Agency has recently devised new tests specifically designed to collect the data necessary for evaluating the hazard inherent in these types of chemical compositions. One of the studies developed by the government for evaluating the overall environmental impact of, for example, a pesticide, is a field dissipation study.

Field dissipation studies are designed to determine the extent of pesticide residue dissipation under actual use conditions. The studies generate data that may be utilized to evaluate the mobility, degradation and dissipation of pesticidal residues.

In order for these studies to accurately reflect actual pesticide residue dissipation in the environment, they, of course, must be conducted in an environment representative of the areas where the pesticide to be tested is expected to be used. This is of critical importance as any number of environmental factors may affect dissipation. Some of these factors include, for example, temperature, rainfall, amount and intensity of sunlight as well as the physical properties and composition of the soil.

Past apparatus and methods that have been developed for completing field dissipation studies have been both relatively expensive and difficult to use. In fact, many past apparatus and procedures have actually promoted mistakes during testing that prevent accurate analytical data to be provided in accordance with the rigid test requirements set by the Environmental Protection Agency. A need is therefore identified for an apparatus and method specifically designed for use in performing field dissipation studies that is relatively simple, inexpensive and effective to utilize.

SUMMARY OF THE INVENTION

Accordingly, it is a primary object of the present invention to provide a method for conducting field dissipation and leachate studies providing better operational integrity and improved results.

Yet another object of the present invention is to provide a method and apparatus for conducting field dissipation studies that are uniquely adapted to provide economical field tests furnishing both reliable and repeatable results.

Still another object of the present invention is to provide a method and apparatus for conducting field dissipation studies also allowing exceedingly accurate prediction of the loss of the composition being tested through volatilization.

An additional object of the present invention is to provide a field testing method and apparatus allowing the collection of all leachate from a soil test zone for subsequent quantitative and qualitative analysis.

Still another object of the invention is to provide an improved field dissipation study method and apparatus allowing full recovery of all test substance including degradates dissipating into the soil in a soil test zone for both quantitative and qualitative analysis.

Additional objects, advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved method is provided for conducting field dissipation and leachate studies of a test substance. The test method utilizes a boundary means, such as a cylindrical column, that is driven into the ground to define within its sidewall a soil test zone. Advantageously, the column is designed so as to achieve this end substantially without disturbing or compacting the soil in the test zone. Thus, the soil in the test zone is as representative as possible of soil in a field to which the substance being tested is expected to be applied. As such, the integrity of the test results is maximized.

After the positioning of the column, the method proceeds with the step of exposing a bottom end of the column which remains undisturbed in place in the ground. Again, this is done substantially without disturbing the soil in the test zone defined by the column.

More particularly, the bottom of the column may be exposed by cutting a trench in the ground adjacent the column. It must be recognized, however, that a sufficient distance is maintained between the trench and the column so as to assure that the column remains undisturbed as the trench is dug to a depth just below the bottom end of the column. Next is the constructing of a lateral passageway connecting the bottom end of the column to the trench. Preferably, this passageway is sufficiently large to allow the placing of a leachate collecting apparatus in the passageway beneath the bottom end of the column. It is this apparatus that collects and holds the leachate from the soil test zone.

In accordance with the further aspects of the method, the method may include the step of shoring the walls of the trench so as to insure that the soil in and around the research area and particularly including the soil test zone remains substantially undisturbed. While shoring may not be necessary in heavy clay soils, it will, of course, be required in loose, sandy soils. Any manner of shoring may be utilized including the placement of plywood along the walls of the trench and the provision of a support frame to hold the plywood in position.

After preparation of the research area as described above, the substance to be tested is applied to the surface of the soil test zone in an appropriate concentration and manner. Additional applications of test substance may also be made over time in accordance with the recommended usage of the test substance by the manufacturer.

At desired intervals during the field dissipation study, it is necessary to recover one or more columns from the ground to determine actual dissipation. This is done by carefully extricating the columns from the ground so that the soil test zone remains substantially intact and undisturbed. Next is the openings of the columns about a longitudinal line. For example, each column may be designed with a longitudinal seam that can be opened. The sidewall of the column is then folded back so as to expose the soil test zone in the form of a core sample.

The core sample is then cut transversely into segments of desired length each representing a particular depth from the soil surface. For example, the first such segment may extend from the surface to a depth of three inches. The second such segment may extend from a depth of three inches to six inches, the third from a depth of six inches to nine inches, and the fourth from a depth of nine inches to twelve inches and so on. Each of the segments is then individually analyzed both quantitatively and qualitatively and compared to a control core sample recovered at the same time and the same manner. The control core sample, however, never received any application of the test substance. Such an analysis allows the presence of the test substance and any resulting degradates to be confirmed at the various soil levels represented by the individual core segments.

From the description of the method above, it should be appreciated that the amount of test substance actually lost through volatilization may also be accurately determined by utilizing the analytical data collected from analysis of the core sample segments and leachate. More specifically, the amount of the test substance actually applied to the soil test zone is recorded. The amount of the test substance recovered in the leachate and the core sample segments including that represented by the presence of degradates is then also determined and recorded. The amount recovered in the leachate and core samples is then subtracted from the amount applied to determine the amount of test substance lost through volatilization. This is a particularly important aspect of the present invention as it eliminates the need to conduct other expensive field studies that would otherwise be necessary to determine the loss of test substance through volatilization.

In accordance with yet another aspect of the present invention, an apparatus is provided for conducting field dissipation studies. As indicated above, the apparatus includes a boundary means, in the form of a cylindrical column, that may be positioned in the ground to define a soil test zone. Preferably, the column is formed from 18 or 20 ga. galvanized steel and has a diameter of 6-10". Advantageously, such a column is sufficiently strong to allow it to be driven into the ground to a sufficient depth to allow completion of the desired studies. In addition, the leading edge of the column is sufficiently thin to cut relatively cleanly through the ground so as to allow the column to be driven into the ground without substantially disturbing or compacting soil in the interior soil test zone.

Preferably, the column is formed with a longitudinal seam where the galvanized steel material is crimped together. Advantageously, when the column is extracted from the ground, this seam may be opened and the sidewall of the column folded back to expose the soil test zone as a complete core. This core may then be sectioned as described above to allow completion of the dissipation studies.

The apparatus also includes a leachate collecting means. The leachate collector may take any form, but preferably includes a funnel having a relatively large upper end. This upper end defines a collection opening which substantially corresponds in size and shape to the bottom end of the column. A container is connected to the bottom end of the funnel. Both the funnel and container are positioned in a passageway directly beneath the column as it is positioned in the ground. More specifically, the collection opening of the funnel is positioned to abut the bottom edge of the column so that any leachate traveling through the soil test zone is collected by the funnel and deposited in the container. The container may then be recovered and the leachate analyzed to determine dissipation of the test substance and the presence of degradates in the leachate.

Still other objects of the present invention will become readily apparent to those skilled in the art from the following description wherein there is shown and described a preferred embodiment of the invention, simply by way of illustration of one of the modes suited to carry out the invention. As it will be realized, the invention is capable of other different embodiments, and its several details are capable of modifications in various, obvious aspects, all without departing from the invention. Accordingly, the drawing and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing:

FIG. 1 is a top plan view of a research site for conducting field dissipation and leachate studies in accordance with the method and apparatus of the present invention;

FIG. 2 is a cross-sectional view along line II—II of FIG. 1; and

FIG. 3 is a cross-sectional view along line III—III of FIG. 1.

Reference will now be made in detail to the present preferred embodiment of the invention, an example of which is illustrated in the accompanying drawing.

DETAILED DESCRIPTION OF THE INVENTION

Reference is now made to FIG. 1 showing a field research site readied in accordance with the teachings of the present invention for conducting field dissipation studies. Field dissipation studies are conducted only at selected sites representative of the areas where the substance to be tested, such as a pestiscide, is expected to be used. The sites are carefully prepared and monitored in order to assure the integrity of the test results.

As best shown in FIG. 1, the field research site 10 includes a series of boundary means or columns 12 that are positioned into the ground G. Preferably, each column 12 is formed from 18 or 20 ga. galvanized steel. Such a column has sufficient strength to allow driving into the ground with, for example, a fence post driver. A removable steel cap (not shown) may, however, also be provided to protect the upper edge of the column from any substantial damage during the driving operation.

The column 12 has a length of anywhere from approximately 1.5-4 feet. The length selected largely is determined by the type of soil in which testing is to be conducted. For example, a shorter column 12 is driven into clay soils where both the depths of probable test substance leaching and column penetration are reduced. In any event, the columns 12 are each driven into the ground until only approximately 1-3" of the upper portion of the column remains exposed above the surface. Then the steel cap is removed.

During the driving operation, it should be appreciated that the leading or bottom edge of the column 12 is sufficiently sharp to cut cleanly through the ground. Thus, the soil held within the interior of the boundary or sidewall of the column 12, forming the soil test zone Z, remains substantially undisturbed and is not compacted. This is a particularly important aspect of the present invention as any change in the density of the soil in the test zone Z from natural conditions could adversely affect the integrity of the test results.

In an effort to further maximize the integrity of the test results, the column 12 is provided with a diameter of between 6-10 inches. Such a relatively large diameter is desired to minimize an effect known as "channeling". More specifically, water has a tendency to seep more quickly and deeply into the ground at the interface of the ground and column sidewall. If a column 12 of smaller diameter were used, test substance would also be drawn deeply into the ground at this interface in an unnatural manner. This, of course, is to be avoided if test results of high integrity are to be obtained. Advantageously, by using a wider diameter column 12 as described and applying the test substance near the center of the soil test zone Z, the potential for this problem effecting test results is minimized.

After the number of columns 12 necessary to conduct a complete field dissipation study are driven into the ground in the form of a row as shown, a trench 14 is cut in the ground parallel to the row. More specifically, the trench 14 is cut adjacent to the columns 12 but spaced sufficiently therefrom so as to ensure that the position of the columns in the ground G remains undisturbed. Again, this is necessary to ensure the integrity of the test results. Where necessary, shoring is utilized to prevent the walls of the trench 14 from caving inward. Thus, as shown in FIGS. 1-3, plywood 16 or other shoring materials may be positioned along the walls of the trench 14. In addition, the necessary framing members 18 in the form of struts and braces may be provided to hold the plywood shoring 16 in position.

The trench 14 is cut deep enough so as to extend in the ground to a depth beneath the bottom end of the columns 12. Following the cutting of the trench 14, is the constructing of a lateral passageway 20 from the trench back into the ground G underneath the columns 12 (see FIGS. 2 and 3). The passageway 20 is constructed sufficiently wide and deep to hold a leachate collecting container 22. Preferably, a collecting funnel 24 is also provided. The funnel 24 includes a relatively large upper end defining a collection opening that substantially corresponds but may be a little wider than the bottom end of the column 12. When placed in proper position, the collection opening of the funnel 24 laps slightly over the entire circumference of the column 12 so that any leachate passing down through the column is collected in the funnel and delivered to the leachate collecting container 22.

After the research site 10 is selected and prepared in accordance with the procedure discussed above, the test substance is applied in an appropriate manner to the soil test zone Z of one or more columns 12. More specifically, the test substance is applied utilizing the method of application stated in the directions for use specified on the product label and at the highest rate recommended on the product label by the manufacturer. Similar follow-up applications at the highest recommended rate are made to the soil test zone Z at the time intervals indicated by the product manufacturer. Throughout the duration of the dissipation studies (a period of anywhere from 3-12 months or more), the leachate collected in the containers 22 is analyzed both quantitatively and qualitatively to determine the presence of test substance and/or test substance degradates.

In addition, leachate from control soil test zones Z is also recovered. No test substance is applied to the control soil test zones. Thus, it is possible to compare leachate collected from control and test substance soil test zones to determine the presence of any unique substances.

In addition to the recovery of the leachate throughout the duration of the studies, soil samples are periodically recovered. For example, soil samples may be recovered the day before the studies begin so as to establish a control. Additional samples may be collected on the day of and the day after application of the test substance. Further samples are taken at increments so that data may be collected to establish patterns of decline of the test substance and patterns of formation and decline of degradation products in the soil. Thus, for example, additional soil samples may be recovered on days 3, 7, 14, 21 and 28. If necessary, further samples may be taken at 2, 3, 6, 9 and 12 months. These, of course, are only approximate times depending, for example, on field accessibility. Further, samplings may be terminated before one year or prolonged depending on the analytical determination of residues.

Soil sampling is accomplished by recovering the columns 12 from the ground G. More specifically, the column selected to be recovered is carefully dug from the ground so as to avoid disturbing other columns 12 in the test site and to maintain the soil test zone Z within the column substantially undisturbed and intact. After recovery of the column 12 is the step of opening the column about a longitudinal line. Preferably, the column 12 includes a folded-over crimped longitudinal seam in the manner of a stovepipe. This seam is opened and the sidewall of the column 12 is folded back so as to expose the soil test zone Z in the form of a core sample. The core sample is then cut into segments of desired depth extending from the top of the soil test zone to the bottom of the soil test zone. For example, a core may be sectioned into a first segment extending from the surface to a depth of 3", a second segment extending from a depth of 3"-6", a third segment extending from a depth of 6"-9", a fourth segment extending from a depth of 9"-12", a fifth segment extending from a depth of 12"-18" and a sixth segment extending from a depth of 18"-24". Each of these segments is then individually analyzed to determine the extent of test substance dissipation and leaching into the soil. Of course, quantitative and qualitative analysis is completed so as to not only determine the presence of the test substance or its degradates, but also the amount of dissipation or leaching and what those degradates are. In addition, soil samples from control test zones Z wherein no test substance has been applied are also periodically recovered for comparison.

Advantageously, with recovery of all the leachate from the soil test zone Z and the analysis of the entire soil test zone for the presence of the test substance and its degradates, the amount of test substance lost through volatilization may also be determined. More specifically, records of the amount of test substance applied to a particular soil test zone Z are maintained. The results of the analysis of the leachate and the recovered soil test zone Z at any particular time may then be utilized to determine the amount of test substance remaining in the soil or the ground water. When this latter amount is subtracted from the total amount applied, the resulting amount is equivalent to the test substance lost through volatilization. Since full recovery from the soil and leachate is possible utilizing the apparatus of the present invention, the determination of the amount of test substance lost through volatilization in this manner is very accurate. As such, some additional and expensive testing to determine loss through volatilization is no longer necessary.

In summary, numerous benefits result from employing the concepts of the present invention. Advantageously, the method and apparatus provide the ability to conduct reliable and economical field dissipation studies. The channeling problem is substantially eliminated and with the full recovery of the leachate from substantially undisturbed soil in the field, the overall integrity of the testing is improved. In fact, the apparatus may be utilized to make an exceedingly accurate prediction of the volatility losses of the test substance in the field.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A method for conducting field dissipation and leachate studies of a test substance utilizing boundary means to define a soil test zone and collecting means for collecting leachate from said soil test zone, comprising the steps of:
positioning said boundary means into the ground; exposing, a bottom end of said boundary means which remains undisturbed in place in said ground substantially without disturbing said soil test zone;
collecting leachate from said soil test zone within said boundary means; and
analyzing said leachate.

2. The method set forth in claim 1 including the step of driving said boundary means into the ground substantially without disturbing or compacting soil in said soil test zone.

3. The method set forth in claim 1, including the step of recovering said boundary means from said ground including said soil test zone substantially intact.

4. The method set forth in claim 3, including the step of opening said recovered boundary means about a longitudinal line and folding said boundary means back so as to expose said soil test zone in the form of a core sample.

5. The method set forth in claim 4, including the step of cutting said core sample into segments of desired depth from a top of said soil test zone to a bottom of said soil test zone.

6. The method set forth in claim 5, including the step of individually analyzing said segments to determine extent of test substance dissipation.

7. The method set forth in claim 6, wherein said analyzing step includes both quantitative and qualitative analysis.

8. The method set forth in claim 7, including the step of determining amount of test substance lost through volatilization by subtracting the amount of test substance recovered in leachate and core sample segments from the amount of test substance applied to said soil test zone.

9. An apparatus for conducting field dissipation and leachate studies of a test substance, comprising: p1 boundary means for positioning into the ground to define a soil test zone, said boundary means being a column that is driven into the ground substantially without disturbing or compacting soil in said soil test zone; and
means for collecting leachate from a bottom end of said boundary means left undisturbed in place in said ground.

10. The apparatus set forth in claim 9, wherein said column is cylindrical.

11. The apparatus set forth in claim 10, wherein said column is formed from 18-20 gauge galvanized steel and has a 6-10 inch diameter.

12. The apparatus set forth in claim 10, wherein said column is formed from galvanized steel and includes a longitudinal seam that may be opened to expose said soil test zone as a complete core when said column is recovered from the ground to determine extent of test substance dissipation.

13. The apparatus set forth in claim 9, wherein said leachate collecting means includes funnel means having a relatively large upper end defining a collection opening substantially corresponding to a bottom end of said boundary means and container means connected to a bottom end of said funnel means for holding leachate collected from said boundary means by said funnel means.

14. A method for conducting field dissipation and leachate studies of a test substance utilizing boundary means to define a soil test zone and collecting means for collecting leachate from said soil test zone, comprising the steps of:
positioning said boundary means into the ground;

exposing a bottom end of said boundary means in said ground substantially without disturbing said soil test zone;
collecting leachate from said soil test zone within said boundary means;
said exposing and collecting steps including the steps of cutting a trench in said ground adjacent said boundary means to a depth below said bottom end of said boundary means; constructing a passageway connecting the bottom end of said boundary means to said trench; and placing said collecting means in said passageway beneath said bottom end of said boundary means so as to collect leachate from said soil test zone; and
analyzing said leachate.

15. The method set forth in claim 14, including the steps of shoring walls of said trench so as to insure soil in and around said boundary means remains substantially undisturbed.

* * * * *